United States Patent [19]

La Via et al.

[11] 4,235,900

[45] Nov. 25, 1980

[54] CEPHRADINE COMPOSITIONS

[75] Inventors: Anthony L. La Via, East Brunswick, N.J.; Irwin S. Gibbs, Philadelphia, Pa.

[73] Assignee: E. R. Squibb & Sons, Inc., Princeton, N.J.

[21] Appl. No.: 960,792

[22] Filed: Nov. 15, 1978

[51] Int. Cl.³ .......................................... A61K 31/545
[52] U.S. Cl. .................................................. 424/246
[58] Field of Search ........................................ 424/246

[56] References Cited

U.S. PATENT DOCUMENTS 3,940,483   2/1976   Dursch ................................. 424/246
3,984,403   10/1976  Fujisawa .............................. 424/246

FOREIGN PATENT DOCUMENTS 2411260   9/1974   Fed. Rep. of Germany ........... 424/246
1291282   10/1972  United Kingdom ..................... 424/246

OTHER PUBLICATIONS

Chem. Abst. 83:152337s, (1975).
Chem. Abst. 86:111175f, (1977).
Chem. Abst. 87:5992f, (1977).
Gallardo, Derwent 13312Y/08, Gall 21.04.75.
Gallardo, Derwent 00582X/01, Gall 16.03.74.
Chem. Abst. 59:6208(c), (1963).
Chem. Abst. 75:40462(g), (1971).

Primary Examiner—Jerome D. Goldberg
Attorney, Agent, or Firm—Lawrence S. Levinson; Burton Rodney

[57] ABSTRACT

Dry solid cephradine compositions are provided comprising cephradine and arginine, for reconstruction as injectables upon addition of water.

A method is also provided for fomulating injectable cephradine.

4 Claims, No Drawings

CEPHRADINE COMPOSITIONS

BACKGROUND OF THE INVENTION

Antibiotics of limited water solubility have been formulated for parenteral application either as aqueous suspensions, or by preparing water soluble derivatives (e.g., salts, esters or complexes) of the parent compound, which upon administration are either in equilibrium with the parent compound, or which are transformed back into the parent compound in the patient's system. Inherent in these practices are several problems. Use of solids in suspension severely limits the mode of parenteral administration. Furthermore, preparation of pharmaceutically acceptable solid derivatives is frequently accompanied by significant yield losses. Moreover, some otherwise desirable derivatives cannot be isolated in suitable form altogether (e.g., in pure crystalline or other stable forms).

U.S. Pat. No. 3,940,483 to Dursch discloses blending solid antibiotics of limited water solubility which are either acidic, basic, or amphoteric in nature (such as cephradine) as dry powders with suitable solid additives, such as alkali metal carbonates, for example sodium carbonate, alkali metal bicarbonates, for example sodium bicarbonate, ammonium carbamate, alkali metal or ammonium phosphates, for example sodium or potassium phosphate, organic amines like N-methylglucamine, tris(hydroxymethyl)aminomethane and the like, alkali metal hydrogen sulfates, for example sodium or potassium hydrogen sulfate, and organic acids like citric acid, tartaric acid or maleic acid. Upon addition of water to such dry mixtures, physiologically acceptable solutions of water soluble salts of the antibiotic are formed in situ and can be administered without delay. However, lactated Ringer's solution must not be used in place of water in formulating injectable cephradine blended with sodium carbonate because a precipitate of $CaCO_3$ can form. Moreover, the sterile cephradine for injection (sodium carbonate blend) has been found to be reasonably well tolerated although there has been some evidence of discomfort on administration.

DESCRIPTION OF THE INVENTION

In accordance with the present invention there is provided dry solid cephradine compositions comprising cephradine and arginine, for reconstitution as injectables upon addition of water as well as lactated Ringer's solution and has demonstrated a much improved local tolerance after intramuscular injection.

The dry cephradine compositions of the invention are stable indefinitely and when formulated for injection may be administered free of pain and are well tolerated without evidence of pain or irritation.

Furthermore, a method is provided for formulating injectable cephradine, which comprises blending cephradine with arginine to provide stable dry mixtures and adding sufficient sterile water thereto to form clear solutions suitable for injection.

The arginine, preferably employed in its L-form, is usually employed in an amount just sufficient to assure complete dissolution of the cephradine upon addition of a small volume of water. This amount may well be less than the stoichiometric quantity required for complete conversion to a salt. The arginine may be employed in a molar ratio to the cephradine in an amount ranging from about 0.5:1 to about 2:1 and preferably from about 1:1 to about 2:1 and in a weight ratio to the cephradine in an amount ranging from about 1:4 to about 1:1.

In forming the injectable solution, sufficient sterile water is added to the solid mixture to provide a concentration of active antibiotic of about 50 to 500 milligrams per milliliter of water, preferably of above 200 milligrams per milliliter of water to 500 milligrams per milliliter of water.

The injectables formulated in accordance with the invention can be employed in the same manner and for the same utility as the parent cephradine.

The formulated cephradine/arginine blend of the invention when administered intramuscularly has been found to achieve peak serum concentrations in about 48 minutes in case of males and 60 minutes in the case of females, comparable to or better than the time to peak serum concentrations observed after oral administration of cephradine capsules. This is indeed surprising and unexpected inasmuch as intramuscular administration of the formulated cephradine/sodium carbonate blend (without arginine) results in time to peak serum concentrations in the case of females of 90 minutes or more and in the case of males of about 66 minutes or more.

The following examples further illustrate the invention. In each example, cephradine is blended with arginine. The mixtures are then combined with small amounts of water and are subsequently gently shaken for about one minute. Clear solutions are obtained in all cases, indicating complete dissolution of the cephradine and suitability of the mixture as an injectable formulation.

EXAMPLE 1

A dry mixture of 250 milligrams α-amino-2,5-dihydrobenzyl-3-desacetoxycephalosporin (cephradine) and of 125 milligrams anhydrous L-arginine is reconstituted with 1.2 milliliters of sterile water. An injectable solution of pH 8.4 is obtained.

EXAMPLE 2

A dry mixture of 250 milligrams of α-amino-2,5-dihydrobenzyl-3-desacetoxycephalosporin (cephradine) and of 250 milligrams of L-arginine is reconstituted with 1.2 milliliters of sterile water to give a clear injectable solution of pH 9.3

EXAMPLE 3

A dry mixture of 250 milligrams of cephradine with 62 milligrams of L-arginine is reconstituted with 7 milliliters of sterile water. An injectable solution of pH 7.5 is obtained.

What is claimed is:

1. A dry solid antibiotic composition suitable for reconstitution as an injectable upon addition of water, which comprises cephradine and arginine, the arginine being present in a weight ratio to the cephradine in an amount ranging from about 1:4 to about 1:1

2. The composition in accordance with claim 1 wherein the arginine is employed in a weight ratio to the cephradine in an amount ranging from about 1:2 to about 1:1.

3. The composition in accordance with claim 1 wherein the arginine is present in a weight ratio to the cephradine of about 1:2.

4. The composition in accordance with claim 1 wherein the arginine is present in a weight ratio to the cephradine of about 1:1.

* * * * *